United States Patent
Aksela et al.

(10) Patent No.: US 6,749,727 B2
(45) Date of Patent: Jun. 15, 2004

(54) HYDROGENATION OF A WORKING SOLUTION IN A HYDROGEN PEROXIDE PRODUCTION PROCESS

(75) Inventors: Reijo Aksela, Espoo (FI); Juhani Paloniemi, Kiviniemi (FI)

(73) Assignee: Kemira Chemicals Oy, Helsinki (FI)

( * ) Notice: Subject to any disclaimer, the term of this patent is extended or adjusted under 35 U.S.C. 154(b) by 94 days.

(21) Appl. No.: 10/096,591

(22) Filed: Mar. 14, 2002

(65) Prior Publication Data

US 2002/0193615 A1 Dec. 19, 2002

(30) Foreign Application Priority Data

Mar. 28, 2001 (FI) .............................. 20010641

(51) Int. Cl.⁷ ............................ C07F 1/00; C07C 29/00
(52) U.S. Cl. ................... 204/157.6; 204/157.9
(58) Field of Search ........................... 204/157.6, 157.9

(56) References Cited

U.S. PATENT DOCUMENTS

| 4,946,566 A | 8/1990 | Stevens et al. | 423/588 |
| 5,785,943 A | 7/1998 | Guillet et al. | 204/157.5 |

FOREIGN PATENT DOCUMENTS

| EP | 0 672 617 A1 | 9/1995 |
| WO | WO95/10480 A1 | 4/1995 |
| WO | WO01/66461 A1 | 9/2001 |

OTHER PUBLICATIONS

Ullman's Encyclopedia of Industrial Chemistry, vol. 13, pp. 447–457, no date.
H. M. Kingston et al.; American Chemical Society; pp. 3–17; 1997, no month.
D. Michael P. Mingos; Chemistry & Industry, Aug. 1, 1994, pp. 596–599.
Loupy et al.; Synthesis, pp. 1213–1234; 1998, no month.
Christopher R. Strauss; Aust. J. Chem., vol. 52, pp. 83–96; 1999, no month.
Sasa Leskovsek et al.; J. Org. Chem., vol. 59, pp. 7433–7436, 1994, no month.
Bimal K. Banik et al.; J. Org. Chem., vol. 64, pp. 5746–5753, no date.
Chemical Abstract, vol. 131, No. 16, Oct. 18, 1999, XP–002238902 p. 656.

*Primary Examiner*—Edna Wong
(74) *Attorney, Agent, or Firm*—Birch, Stewart, Kolasch & Birch, LLP

(57) ABSTRACT

A method of hydrogenating alkyl anthraquinones and/or alkyl hydroanthraquinones to alkyl anthrahydroquinones and/or alkyl hydroanthrahydroquinones is disclosed. The reaction is carried out in the presence of a catalyst under electromagnetic irradiation, such as microwave irradiation. The invention further relates to a method of hydrogenating a working solution in a hydrogen peroxide production process, wherein the working solution contains alkyl anthraquinones and/or alkyl hydroanthraquinones dissolved in at least one solvent to convert the quinines to the corresponding alkyl anthrahydroquinones and/or alkyl hydroanthrahydroquinones, where the reaction is carried out in the presence of a catalyst under electromagnetic irradiation such as microwave irradiation.

17 Claims, No Drawings

HYDROGENATION OF A WORKING SOLUTION IN A HYDROGEN PEROXIDE PRODUCTION PROCESS

BACKGROUND OF THE INVENTION

1. Field of the Invention

The present invention relates to a method of hydrogenation of alkyl anthraquinones and/or alkyl hydroanthraquinones in the presence of a catalyst. More specifically, the present invention relates to a hydrogenation method of a working solution in a hydrogen peroxide production process utilizing an anthraquinone method.

2. Description of the Prior Art

In industrial scale, hydrogen peroxide is mainly produced by an anthraquinone process. In this method anthraquinones which are dissolved in an appropriate organic solvent, are used as a reaction media. The organic solvent is usually a mixture of several organic solvents. The solution obtained by dissolving the anthraquinones in the organic solvent is called "a working solution".

The anthraquinones (AQ) in the working solution are subjected to reduction with hydrogen (hereinafter referred to as "the hydrogenation") in the presence of a catalyst (reaction 1) to produce corresponding anthrahydroquinones (AHQ).

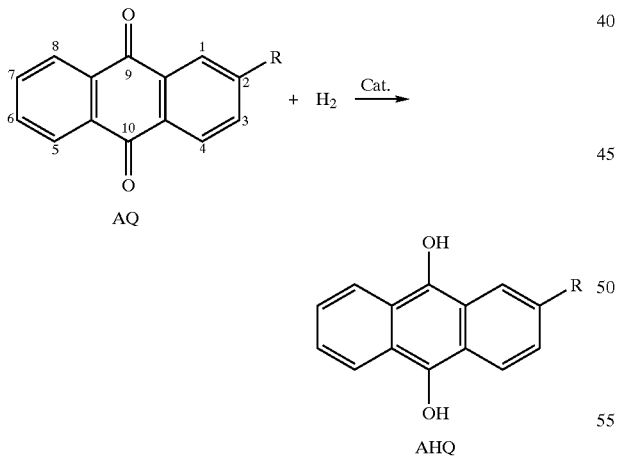

R = alkyl

Thereafter the anthrahydroquinones are oxidized with air or with an oxygen-containing mixture of gases to convert the anthrahydroquinones into the anthraquinones again (reaction 2). In this oxidation step one mole of hydrogen peroxide is formed per one mole of oxidized anthrahydroquinone.

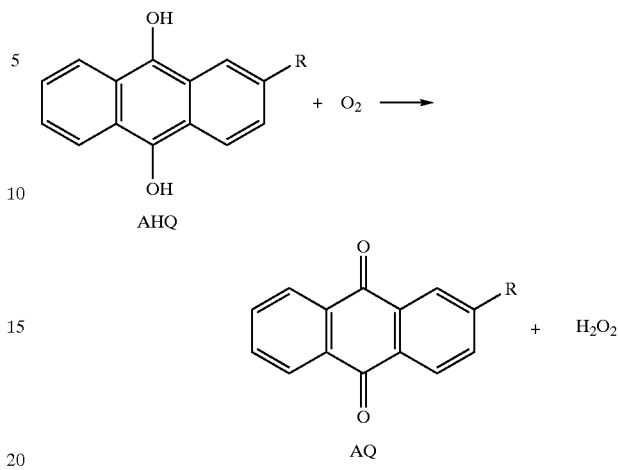

Hydrogen peroxide produced into the working solution after the above mentioned process steps is usually separated from the working solution by extraction with water.

The working solution from which hydrogen peroxide has been separated is returned to the reduction step again, thereby forming a cyclic process. This process can produce hydrogen peroxide substantially from hydrogen and air, and hence it is an extremely efficient process.

The alkyl anthrahydroquinones (AHQ) and the alkyl anthraquinones (AQ) are subjected to a number of secondary reactions during the cyclic process. Hydrogenation of the aromatic nuclei of the alkyl anthraquinones yields alkyl tetrahydroanthrahydroquinones (THAHQ's or "tetra") (see reaction 3). THAHQ's have an ability to produce hydrogen peroxide by the repetition of the reduction and oxidation like the alkyl anthraquinones.

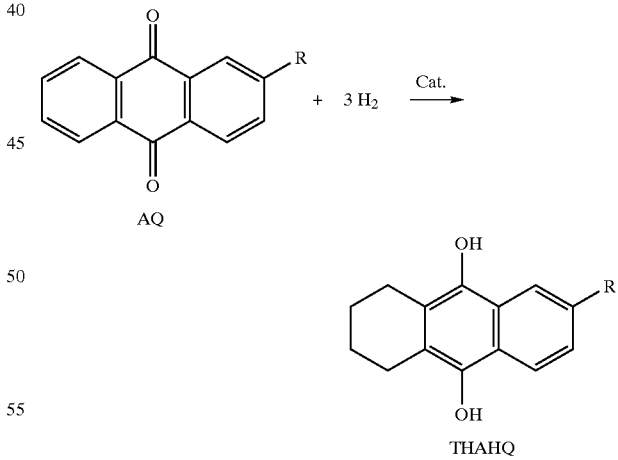

If "tetra" formation is not suppressed during hydrogenation or "tetra" is not dehydrogenated, an equilibrium is reached, in which the hydroquinone charged to the oxidizer consists exclusively of 2-alkyl-5,6,7,8-tetrahydroanthrahydroquinone (THAQ). Such a system is called an "all-tetra" system. Even in the all-tetra system it is essential to maintain a certain equilibrium between AQ:s and THAQ:s in order to avoid the formation of further by-products.

The cyclic Riedel-Pfleiderer or BASF process forms the technological basis for all modern AQ processes. The processes are described for example in *Ullman's Encyclopedia of Industrial Chemistry*, vol. A 13, pp. 447–457 (VCH, Weinheim, 1989). Developments include improvement of the individual process steps, use of stable working solutions, and use of selective hydrogenation catalysts.

The basic principles of the process are:

Hydrogenation. From the storage tank or hydrogenation feed tank, the working solution enters the hydrogenator where it is hydrogenated in the presence of a suspended, supported, or fixed-bed catalyst. If a suspended catalyst (e.g., palladium black or Raney nickel) or a supported catalyst (e.g., palladium) is used, the hydrogenation step includes a main filtration stage which retains the catalyst and allows it to be returned to the hydrogenator.

Oxidation. Before the hydrogenated working solution that contains hydroquinone can be fed to the oxidation step, it must pass through a safety filtration stage. This is particularly important because the hydrogenation catalysts used in the AQ process (palladium and Raney nickel) also catalyze the decomposition of hydrogen peroxide. Even a small amount of these catalysts in the oxidation and extraction steps would lead to considerable loss of hydrogen peroxide and serious disturbances. During the oxidation step, the hydrogenated working solution is gassed with air and/or oxygen. Dissolved hydroquinones are oxidized to quinones, and hydrogen peroxide is formed.

Extraction and Recovery of the Working Solution. The oxidized working solution is then treated with water to extract hydrogen peroxide. The working solution leaving the extraction unit must be adjusted to a specific water content before being returned to the hydrogenation step. Free water taken up by the working solution during extraction is separated and the water content is adjusted to the desired level in the drier.

Hydrogen Peroxide Concentration. Crude aqueous hydrogen peroxide from the extraction stage ($H_2O_2$ concentration 15–35 wt %) is fed into the crude product storage tank via a prepurification unit. From the crude product storage tank, aqueous hydrogen peroxide goes to the concentration unit where it is distilled. Here, hydrogen peroxide is freed from most of its impurities and concentrated to the commercial concentration of 50–70 wt %; it is then collected in a storage container.

Auxiliary Processes. A number of additional processes are required to maintain the AQ operation. For example, to maintain hydrogenation activity, part of the catalyst is removed, regenerated in the catalyst regeneration area, and returned to the hydrogenator. To compensate for quinone and solvent losses, working solution is periodically made up with anthraquinone and solvent.

Hydrogenation Step

The hydrogenation step is the most important step of modern AQ processes. Quinone decomposition products that cannot be regenerated into active quinone are formed during this step. New hydrogenation catalysts and hydrogenation reactors have been developed that deviate totally from the BASF principle. Here, design of the hydrogenator depends largely on the type of catalyst used.

Four typical reactors for the three usual catalyst systems (suspended, supported, and fixed-bed catalysts) are discussed.

BASF Hydrogenation Step. The hydrogenation step in the BASF plant uses a Raney nickel catalyst at a slight excess pressure of approximately 0.2 MPa and at 30–36° C. Because Raney nickel is sensitive to oxygen, the working solution from the extraction or drying and purification steps cannot be fed directly into the hydrogenator. This working solution still contains residual hydrogen peroxide and must pass over a decomposition catalyst (e.g., supported Ni—Ag), together with a fraction of the hydrogenated working solution (which also contains hydroquinone), to remove hydrogen peroxide completely:

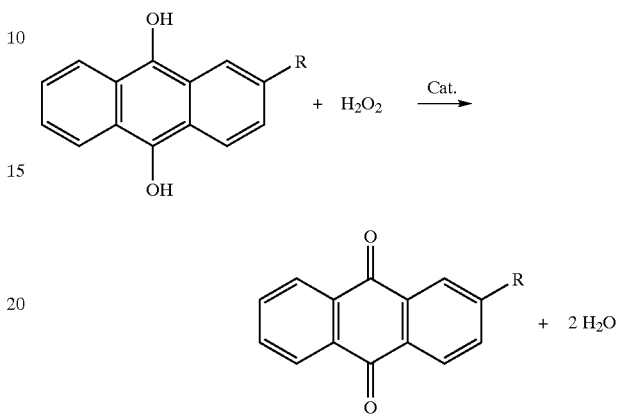

The solutions are passed through the precontact column and collected in the hydrogenator feed tank. The working solution is then pumped into the stirred vessel reactor and is gassed with hydrogen in the presence of Raney nickel. Periodic addition of small amounts of hydrogenation catalyst from the catalyst feed tank allows a constant rate of hydrogen conversion in the hydrogenator. Hydrogenated working solution is collected in the oxidizer feed tank through the internal filters in the stirred vessel, thus exploiting the excess pressure in the reactor. The solution is then led into the oxidation step via the safety filter. A side stream of hydrogenated working solution is withdrawn and recycled to the precontact column.

When the concentration of Raney nickel in the hydrogenation reactor reaches a certain limit, the content of the reactor is drained into the catalyst separator. Raney nickel settles to the bottom, and catalyst-free supernatant is pumped back to the hydrogenator.

A significant disadvantage of Raney nickel as catalyst is its limited selectivity, i.e., the ratio of hydroquinone formation to "tetra" formation. BASF largely eliminated this by pretreating the catalyst with ammonium formate.

Alternatives were subsequently suggested for pretreating Raney nickel (e.g., nitrites, amines, and aldehyde solutions).

The pyrophoric properties of Raney nickel also require more stringent safety procedures when handling the material. Raney nickel is still used today in some AQ plants, but palladium catalysts are preferred because of their higher selectivity and simpler handling.

Degussa Hydrogenation Step. Degussa has proposed the use of palladium black as the hydrogenation catalyst. This exploits the advantages offered by a suspended catalyst and avoids the disadvantages of Raney nickel. Equipment that allows good conversion of hydrogen with very finely distributed palladium black.

The most important feature of the loop reactor is the connection in series of pipes with different diameters. The working solution flows downward in the large pipes at a rate of 0.7–1.5 m/s and flows upward in the narrower pipes at 1.5–3 m/s.

Degussa proposed a carbon filter. A decline in filter performance can be overcome by periodic back flush with hydrogenated working solution through the filter into the hydrogenator.

Advantages of this hydrogenation system are 1) almost complete conversion of hydrogen,
2) nonpyrophoric catalyst,
3) easy exchange of palladium black, and
4) easy regeneration of the catalyst.

Laporte Hydrogenation Step. Laporte Chemicals and other companies proposed the use of supported palladium catalysts. These catalysts have the advantage that their particle diameter of 0.06–0.15 mm makes their filtration and recirculation to the reactor simpler than those of palladium black.

Laporte proposed an apparatus for industrial hydrogenation. The reactor contains a series of tubes whose lower ends lie just above the bottom of the reactor and whose top ends are just below the liquid surface. Hydrogen is fed into the bottom of each tube, and very small gas bubbles are formed by distributors. Upward flow occurs in the tube due to the density difference between the solutions in the tube and in the reactor. The catalyst suspension is drawn into the pipe by the continuous flow of working solution. To obtain a sufficiently high airlift effect in the tube, hydrogen must be circulated continuously.

FMC Hydrogenation Step. Fixed-bed hydrogenation represents a simple solution for the hydrogenation step; it involves a palladium catalyst and avoids the problem of filtration and recirculation of catalyst into the reactor. The first industrial fixed-bed hydrogenation unit for the AQ process was commissioned by FMC.

The fixed-bed catalyst should have a diameter of 0.2–5 mm, a surface area less than 5 $m^2/g$, and a pore volume smaller than 0.03 $cm^3/g$. The working solution is pumped to the top of the reactor. A side stream of the hydrogenated working solution is also fed into the fresh working solution after the heat of reaction has been removed in a heat exchanger. This operation results in optimal cross-sectional loading of the fixed bed, which should be 12–120 $m^3$ of working solution per square meter per hour. The catalyst must fulfil a number of requirements such as 1) high abrasion resistance to allow simplification of the filtration step,
2) a long working life because replacing a fixed-bed catalyst is more complicated than replacing a suspended catalyst,
3) good productivity, and
4) easy regeneration of the catalyst.

SUMMARY OF THE INVENTION

The objective of the present invention is to obtain a more effective method of hydrogenating the alkyl anthraquinones in the preparation of hydrogen peroxide using the anthraquinone process.

It is known from the recent literature concerning organic synthesis that the reaction times of organic reactions are remarkable reduced when the energy necessary for the occurrence of the reaction is introduced to the system by using electromagnetic irradiation.

For example, the principles of the use of microwave irradiation in chemistry are described in detail for example in the book "Microwave-Enhanced Chemistry, fundamentals, sample preparation and applications" edited by H. M. Kingston and S. J. Haswell (American Chemical Society 1997). The microwave region in the electromagnetic spectra corresponds to the wavelengths 1–100 cm and the frequencies from 30 GHz to 300 MHz, respectively. According to an international agreement, the frequencies 6.78 MHz, 13.56 MHz, 27.12 MHz, 40.68 MHz, 915±25 MHz, 2450±13 MHz, 5800±75 MHz and 22125±125 MHz of the electromagnetic irradiation are committed to industrial and scientific use. The apparatus generating microwave energy is called a magnetron or a klystron. The commonly used magnetrons operate at 2.45 GHz frequency corresponding a wavelength of 12.2 cm, whereas klystrons operate at 915 MHz frequency corresponding a wavelength of 32.8 cm.

There is a wide and continuously increasing literature available in the area of using microwave techniques in organic synthesis. An example of a short summary article of this topic was published by Mingos in 1994 (D. Michael P. Mingos; "Microwaves in chemical synthesis" in *Chemistry and industry* 1. August 1994, pp. 596–599). Loupy et. al. have recently published a review concerning heterogenous catalysis under microwave irradiation (Loupy, A., Petit, A., Hamelin, J., Texier-Boullet, F., Jachault, P., Mathe, D.; "New solvent-free organic synthesis using focused microwave" in *Synthesis* 1998, pp. 1213–1234). Another representative article of the area is published by Strauss (C. R. Strauss; "A combinatorial approach to the development of Environmentaly Benign Organic Chemical Preparations", an invited review in *Aust. J. Chem.* 1999, 52, 83–96).

Several applications of electromagnetic radiation to catalytic hydrogenation appear in the recent literature. Leskovsek et al. report a remarkable shortening in the reaction times of catalytic hydrogenation of soybean oil in their article "Kinetics of Catalytic Transfer Hydrogenation of Soybean Oil in Microwave and Thermal Field" in J. Org. Chem. (1994), 59(24), 7433–6. In this application, the reaction times were shortened to ⅛ of those obtained by using conventional techniques.

Banik et al. report catalytic hydrogenations in high boiling solvent in the article "Microwave-Assisted Rapid and Simplified Hydrogenation" J. Org. Chem. (1999), 64(16), 5746–5753. Rapid reduction of double bonds and hydrogenolysis of several functional groups were obtained by using 10% palladium on carbon as catalyst.

In the course of an intensive research work, the inventors have found, that the hydrogenation of the working solution of hydrogen peroxide process by using a heterogenous catalyst, is remarkably improved when the reaction is performed under electromagnetic irradiation.

DETAILED DESCRIPTION OF THE PRESENT INVENTION

In a first aspect of the present invention there is provided a method of hydrogenation of alkyl anthraquinones and/or alkyl hydroanthraquinones to alkyl anthrahydroquinones and/or alkyl hydroanthrahydroquinones, wherein the reaction is carried out in the presence of a catalyst under electromagnetic irradiation.

In a second aspect of the invention there is provided a method of hydrogenating a working solution in a hydrogen peroxide production process, said working solution containing alkyl anthraquinones and/or alkyl hydroanthraquinones dissolved in at least one solvent, to convert said quinones to corresponding alkyl anthrahydroquinones and/or alkyl hydroanthrahydroquinones, wherein the reaction is carried out in the presence of a catalyst under electromagnetic irradiation.

Preferably said working solution to be hydrogenated is formed during the production of hydrogen peroxide by a cyclic process including alternate hydrogenation and oxidation of the working solution.

Thus, according to the method of the present invention an alkyl anthraquinone can be hydrogenated to the corresponding alkyl anthrahydroquinone and/or an alkyl tetrahydroanthraquinone can be hydrogenated to the corresponding alkyl tetrahydroanthrahydroquinone.

The frequency of the electromagnetic irradiation can be selected from the frequencies 6.78 MHz, 13.56 MHz, 27.12 MHz, 40.68 MHz, 915 MHz and 2450 MHz.

The electromagnetic energy is preferably introduced at the frequency of about 2450 MHz or 915 MHz. The power level can be for example within the range from 10 W to 2000 kW.

The electromagnetic irradiation is preferably microwave irradiation.

The method of the present invention for hydrogenating alkyl anthraquinones and/or alkyl hydroanthraquinones under electromagnetic irradiation is applicable to working solutions where 2-amyl anthraquinone (e.g. 2-sec.amyl anthraquinone), 2-methyl anthraquinone, 2-ethyl anthraquinone, 2-isopropyl anthraquinone, 2-butyl anthraquinone (e.g. 2-isobutyl anthraquinone or 2-t-butyl anthraquinone), 1,3-diethyl anthraquinone, 2,3-dimethyl anthraquinone, 1,4-dimethyl anthraquinone, 2,7-dimethyl anthraquinone or combinations of the above mentioned anthraquinones, or the corresponding hydroanthraquinones, such as tetrahydroanthraquinones are used as a reaction media in the preparation of hydrogen peroxide. The most preferred anthraquinones are 2-ethyl, 2-amyl and 2-t-butyl anthraquinones.

The method of the present invention for hydrogenation of alkyl anthraguinones to alkyl anthrahydroquinones under electromagnetic irradiation is applicable to working solutions where aromatic hydrocarbons, organic phosphates, alkylated ureas, organic carboxylic acid esters, alcohols, or alkyl carbamates are used as solvents of the anthraquinones or anthrahydroquinones. More preferably, the method is applicable to the hydrogenation of working solutions where an aromatic crude oil distillate from the boiling point range of from 100° C. to 250° C. is used as the main anthraquinone solvent and a tetra-alkylated urea derivative or a trialkyl phosphate or an alkyl carbamate or a combination thereof is used as the main anthrahydroquinone solvent.

As an example of aromatic solvents can be mentioned commercial crude oil distillates (trade names Shellsol A, Shellsol AB, Shellsol NF, Exxon Solvesso or SureSol). As examples of suitable anthrahydroquinone solvents can be mentioned tetrabutylurea, cyclic urea derivatives, 2-ethylhexyl phosphate, tributyl phosphate and trioctyl phosphate. In addition carboxylic acid esters, for example methyl cyclohexyl acetate, and $C_4$–$C_{12}$ alcohols are suitable anthrahydroquinone solvents. As a suitable aliphatic alcohol, 2-ethylhexanol can be mentioned.

The hydrogenation method of the present invention can be carried out in a slurry reactor, fixed bed reactor, fluidized bed reactor, batch reactor or continuous flow reactor.

The hydrogenation method of the present invention can be carried out by using any material capable of catalyzing hydrogenation reaction. Preferred catalysts are palladium, rhodium, and nickel catalysts as solid metals or as special catalysts supported on a solid support material, preferably on carbon, alumina or zeolites. In the latter case the catalysts are preferably prepared by impregnating the above mentioned metal catalysts to the support material.

The present invention is based on electromagnetic, preferably microwave enhanced hydrogenation of the working solution of a hydrogen peroxide production process. The method of the present invention is superior compared to the existing techniques because the reaction rate of the hydrogenation reaction is remarkably enhanced. Therefore, the amount of palladium or other hydrogenation catalyst needed for the production of hydrogen peroxide could be remarkably diminished when the hydro-genation is performed under electromagnetic irradiation. This will result in savings in costs of production of the hydrogen peroxide.

The invention is described by the following example. However, this example does not limit the invention.

EXAMPLE 1

A working solution withdrawn from a hydrogen peroxide process was hydrogenated either under microwave irradiation or under conventional heating with a water bath at 50° C. in a stirred reactor.

When using microwave irradiation for heating up the reaction mixture, reflected and input powers and temperature was recorded. When microwave irradiation was applied, the reaction temperature was limited to 50° C. and the microwave power was adjusted only to reach and maintain this reaction temperature. For conventional heating, only temperature was recorded.

Thus, 50 g of a working solution containing

| | |
|---|---|
| 2-ethyl anthraquinone (EAQ) | 3.1% w/w |
| tetrahydro 2-ethyl anthraquinone (THEAQ) | 5.1% w/w | dissolved in a mixture of an aromatic hydrocarbon solvent (70% v/v) and a mixture of tetrabutyl urea and trioctylphosphate (30% v/v) was placed in a glass-tube reactor equipped with a stirrer. The catalyst, palladium on carbon (5% Pd/C) was added with mixing. When the temperature of the working solution was settled to 50° C., hydrogenation was carried out at 2 bar (0.2 MPa) absolute hydrogen gas pressure for one hour by stirring the reaction mixture at 1000 rpm stirring speed. After the hydrogenation reaction, the working solution containing anthrahydroquinones, was filtered through an ultra fine filtering paper under nitrogen. Then, a 5 mL sample of the filtered working solution, was oxidized during 20 minutes with an air flow at 50° C. This sample was weighted and hydrogen peroxide was extracted with 50 mL of 0.5 N sulphuric acid. A constant volume of the aqueous phase (Vaq) was diluted in 2N sulphuric acid and the concentration of hydrogen peroxide was determined by a titration with potassium permanganate solution.

The experimental results are presented in Table 1.

TABLE 1

| Experiment | Catalyst (g) | Heating | Conc. of $H_2O_2$ in water after extraction (wt %) | Observations |
|---|---|---|---|---|
| 1 | 2.5 | Conventional | 0.15 | |
| 2 | 2.5 | Microwave | 0.23 | Hydroquinone precipitate |
| 3 | 0.5 | Microwave | 0.21 | Hydroquinone precipitate |
| 4 | 0.125 | Microwave | 0.30 | Hydroquinone precipitate |

The $H_2O_2$ content of solution in experiment 2 was 48% higher than in the comparative experiment 1, where ordinary heating was used. The $H_2O_2$ titration was performed from a clear sample withdrawn from the reaction mixture after hydrogenation. However, precipitation was obtained in the reactor in experiments 2–4. This precipitate was later detected to be 2-ethyl anthrahydroquinone. Because anthrahydroquinones are less soluble to the working solution, this is a typical phenomena of an "over hydrogenation". This indicates that the real anthrahydroquinone content was much higher than even the analyzed value.

This example clearly shows the effectiveness of using MW technique in the hydrogenation step.

In experiments 3 and 4, the amount of catalyst was diminished to 20% or 5% of the original amount, respectively. However, the hydrogen peroxide content after oxidation was comparable to the one in experiment 2. Moreover, anthrahydroquinone precipitate was observed also in those samples indicating that the actual degree of hydrogenation was much higher than the one detected by titration.

These examples clearly show the advantage of using electromagnetic irradiation in the hydrogenation step. The hydrogenation step is remarkably enhanced establishing similar degree of hydrogenation by using only 5% of the amount of the catalyst necessary for obtaining the same result by using conventional hydrogenation.

What is claimed is:

1. A method of hydrogenating alkyl anthraquinones and/or alkyl hydroanthraquinones to alkyl anthrahydroquinones and/or alkyl hydroanthrahydroquinones, said method comprising contacting said alkyl anthraguinones and/or alkyl hydroanthraguinones under hydrogenation conditions in the presence of a hydrogenation catalyst under microwave radiation.

2. The method of claim 1, wherein an alkyl anthraquinone is hydrogenated to the corresponding alkyl anthrahydroquinone.

3. The method of claim 1, wherein an alkyl tetrahydroanthraquinone is hydrogenated to the corresponding alkyl tetrahydroanthrahydroquinone.

4. The method of any of claims 1 to 3, wherein the alkyl anthraquinone is selected from the group consisting of 2-ethyl, 2-amyl and 2-t-butyl anthraquinones and mixtures thereof, and the alkyl hydroanthraquinone is selected from the group consisting of 2-ethyl, 2-amyl and 2-t-butyl hydroanthraquinones and mixtures thereof.

5. The method of claim 1, wherein the frequency of the microwave irradiation is selected from the frequencies 915 MHz or 2450 MHz.

6. The method of claim 1, wherein the catalyst is selected from the group consisting of palladium, rhodium and nickel catalysts.

7. The method of claim 6, wherein the catalyst is in the form of a solid metal or is supported on a solid support material selected from the group consisting of carbon, alumina or zeolite.

8. A method of hydrogenating a working solution in a hydrogen peroxide production process, said working solution containing alkyl anthraquinones and/or alkyl hydroanthraquinones dissolved in at least one solvent, to convert said quinones to corresponding alkyl anthrahydroquinones and/or alkyl hydroanthrahydroquinones, wherein said method is carried out in the presence of a hydrogenation catalyst under microwave irradiation.

9. The method of claim 8, wherein the working solution to be hydrogenated is formed during the production of hydrogen peroxide by a cyclic process including alternate hydrogenation and oxidation of the working solution.

10. The method of claim 8 or 9, wherein the working solution to be hydrogenated contains alkyl tetrahydroanthraquinones which are hydrogenated to the corresponding alkyl tetrahydroanthrahydroquinones.

11. The method of claim 8, wherein the alkyl anthraquinone is selected from the group consisting of 2-ethyl, 2-amyl and 2-t-butyl anthraquinones and mixtures thereof, and the alkyl hydroanthraquinone is selected from the group consisting of 2-ethyl, 2-amyl and 2-t-butyl hydroanthraquinones and mixtures thereof.

12. The method of claim 8, wherein the solvent is selected from the group consisting of aromatic hydrocarbons, organic phosphates, alkylated ureas, organic carboxylic acid esters, alcohols, alkyl carbamates and mixtures thereof.

13. The method of claim 12, wherein the solvent comprises a mixture of a first solvent comprising an aromatic hydrocarbon, and a second solvent selected from the group consisting of tetra-alkylated urea derivatives, trialkyl phosphates and alkyl carbamates and mixtures thereof.

14. The method of claim 8, wherein the hydrogenation is carried out in a slurry reactor, fixed bed reactor, fluidized bed reactor, batch reactor or continuous flow reactor.

15. The method of claim 8, wherein the frequency of the microwave irradiation is selected from the frequencies 915 MHz or 2450 MHz.

16. The method of claim 8, wherein the catalyst is selected from the group consisting of palladium, rhodium and nickel catalysts.

17. The method of claim 16, wherein the catalyst is in the form of a solid metal or is supported on a solid support material selected from the group consisting of carbon, alumina or zeolite.

* * * * *